United States Patent
Ragoonath

(10) Patent No.: US 10,201,486 B2
(45) Date of Patent: Feb. 12, 2019

(54) METHOD OF MAKING A HAIR GROWTH PRODUCT

(71) Applicant: Sidiram S. Ragoonath, Dallas, TX (US)

(72) Inventor: Sidiram S. Ragoonath, Dallas, TX (US)

(*) Notice: Subject to any disclaimer, the term of this patent is extended or adjusted under 35 U.S.C. 154(b) by 0 days.

(21) Appl. No.: 15/278,134

(22) Filed: Sep. 28, 2016

(65) Prior Publication Data

US 2017/0172878 A1 Jun. 22, 2017

Related U.S. Application Data

(63) Continuation-in-part of application No. 14/973,368, filed on Dec. 17, 2015, now abandoned.

(51) Int. Cl.

| | | |
|---|---|---|
| A61K 8/42 | (2006.01) | |
| A61K 8/44 | (2006.01) | |
| A61K 8/41 | (2006.01) | |
| A61K 8/23 | (2006.01) | |
| A61K 8/55 | (2006.01) | |
| A61K 8/34 | (2006.01) | |
| A61K 8/92 | (2006.01) | |
| A61K 8/27 | (2006.01) | |
| A61K 8/24 | (2006.01) | |
| A61K 8/19 | (2006.01) | |
| A61K 8/20 | (2006.01) | |
| A61Q 7/00 | (2006.01) | |
| A61K 8/04 | (2006.01) | |
| A61F 13/40 | (2006.01) | |
| A61K 8/9711 | (2017.01) | |

(52) U.S. Cl.
CPC ............ *A61K 8/42* (2013.01); *A61K 8/042* (2013.01); *A61K 8/19* (2013.01); *A61K 8/20* (2013.01); *A61K 8/23* (2013.01); *A61K 8/24* (2013.01); *A61K 8/27* (2013.01); *A61K 8/34* (2013.01); *A61K 8/416* (2013.01); *A61K 8/44* (2013.01); *A61K 8/55* (2013.01); *A61K 8/922* (2013.01); *A61K 8/9711* (2017.08); *A61M 35/006* (2013.01); *A61Q 7/00* (2013.01); *A61K 2800/49* (2013.01); *A61K 2800/596* (2013.01); *A61K 2800/70* (2013.01); *A61K 2800/87* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 3,915,686 A * | 10/1975 | Miller | ............ C05F 11/00 47/59 R |
| 4,206,195 A | 6/1980 | Bolich, Jr. et al. | |
| 4,206,196 A | 6/1980 | Davis | |
| 4,614,200 A | 9/1986 | Hsiung et al. | |
| 4,895,722 A | 1/1990 | Abe et al. | |
| 4,960,588 A | 10/1990 | Hoshowski et al. | |
| 5,236,950 A | 8/1993 | Aoyama et al. | |
| 5,368,850 A | 11/1994 | Cauwet et al. | |
| 5,595,727 A | 1/1997 | Sturla | |
| 5,932,251 A | 8/1999 | Kirkpatrick | |
| 6,743,756 B2 | 6/2004 | Harris, Jr. | |
| 6,800,276 B2 | 10/2004 | Kim et al. | |
| 8,715,714 B2 | 5/2014 | Kim et al. | |
| 8,865,144 B2 | 10/2014 | Constantinides et al. | |
| 2007/0231377 A1 | 10/2007 | Abou-Nemeh | |
| 2008/0275118 A1 | 11/2008 | Shaw et al. | |
| 2011/0195039 A1 | 8/2011 | Isaacs | |
| 2012/0263660 A1 | 10/2012 | Altschul et al. | |
| 2013/0115183 A1 | 5/2013 | Ko | |
| 2014/0260470 A1 * | 9/2014 | Taulbee | ............ C05C 1/02 71/30 |
| 2015/0079141 A1 | 3/2015 | Wingfield | |
| 2016/0000093 A1 * | 1/2016 | Lamb | ............ A01N 65/22 504/101 |

FOREIGN PATENT DOCUMENTS

WO WO-2011000061 A1 * 1/2011 ............ C05D 9/02

OTHER PUBLICATIONS

Kmart "Miracle Grow 1001122 Miracle-Gro® Water Soluble All Purpose Plant Food 1.5 lbs.," Feb. 8, 2012; http://www.kmart.com/miracle-grow-plant-food-all-purpose-water-soluble/p-043W043077211000P.*
Shop your Way, "The Scotts Co.: African Violet Food," Feb. 8, 2012; https://www.shopyourway.com/the-scotts-co-african-violet-food/438368991.*
Houzz "Do All houseplants need distilled water to do well??," Sep. 30, 2009; http://forums2.gardenweb.com/discussions/1485622/do-all-houseplants-need-distilled-water-to-do-well.*
Barthelow "5 Creative uses for seaweed in the home," Sep. 2, 2015; https://www.rodalesorganiclife.com/garden/5-creative-uses-for-seaweed-in-the-home.*

* cited by examiner

*Primary Examiner* — David J Blanchard
*Assistant Examiner* — Alissa Prosser
(74) *Attorney, Agent, or Firm* — Hemingway & Hansen, LLP; D. Scott Hemingway

(57) ABSTRACT

A composition and method for treating hair loss is disclosed. The composition comprises water-soluble ionizable metal and non-metal components, aqueous and alcohol-based solvents, potassium iodide and citrus essential oil, and is preferably provided as a non-aerosol spray product that is applied to the hair and scalp. The invention further provides a method of making and using the composition.

7 Claims, 2 Drawing Sheets

METHOD OF MAKING A HAIR GROWTH PRODUCT

CROSS REFERENCE TO RELATED APPLICATIONS

This application is a continuation-in-part of U.S. application Ser. No. 14/973,368, filed Dec. 17, 2015.

STATEMENT REGARDING FEDERALLY SPONSORED RESEARCH OR DEVELOPMENT

Not applicable.

TECHNICAL FIELD OF INVENTION

This invention relates to the field of treatment of hair loss.

BACKGROUND OF THE INVENTION

Hair loss is a common condition in humans. While not a physically injurious condition, hair loss can be a source of stress or anxiety for many individuals. There are numerous causes for hair loss including heredity, nutritional deficiencies, hormone imbalances, auto-immune disorders, chemotherapy, and stress, among others. Methods to remedy hair loss have involved treatments of antimicrobial compositions, aromatic oils, cortisol blockers, nutritional supplements, treatments to improve the appearance of thinning hair and many other treatment compositions.

The hair loss remediation methods have varying levels of success depending on the primary reason for the hair loss in the individual along with the compliance of the individual in using a particular remedy for the requisite period. There are many potential causes of hair loss, which means there also are many potential routes to remedy each cause of hair loss.

For instance, some remedies may provide vitamin, mineral or oil supplements to the body, which can enhance hair growth retarded by certain hair loss problems. Also, compliance with a method of treatment can be a factor for many individuals. Treatments that promote hair growth generally take a number of months to achieve the desired results due to the length of time associated with hair growth and rest cycles. Products which are difficult or unpleasant to use may cause an individual to stop using a potentially effective composition before the composition has had adequate time to work. Difficulties, such as complicated application procedures, products that make the hair greasy or hard to style, products that make the scalp area itch or that have an unpleasant odor, are all reasons an individual might not continue to use a hair loss remedy.

Many compositions and methods have been suggested to remedy hair loss by promoting hair growth and/or enhancing the appearance of hair. These known methods include the following prior art references.

U.S. Patent Publication No, 2015/0079141 to Wingfield is entitled "Chelated Metal Oxide Gel Compositions" and describes a composition of chelated metals that has antimicrobial and antiviral effects primarily utilizing chelated silver oxide along with other antimicrobial ingredients which may be included in many types of products including products for hair.

U.S. Patent Application Publication No. 2013/0115183 to Ko is entitled "Method of Preparing Hair and Scalp Conditioning Compositions including Aromatic Oil Blend with Enhanced Efficacy" and describes the use of a combination of aromatic oils for prevention of hair loss.

U.S. Patent Application Publication No. 2012/0263660 to Altschul et al. is entitled "Hair Loss Treatment" and describes the use of cortisol blockers for prevention of stress induced hair loss.

U.S. Patent Application Publication No. 2011/0195039 to Isaacs is entitled "Hair Building Solid Agent" and describes a hair spray composition that electrostatically binds to the hair to achieve a thickened appearance.

U.S. Patent Application Publication No. 2008/0275118 to Shaw et al. is entitled "Health and Cosmetic Composition and Regime for Stimulating Hair Growth and Thickening on the Head, Including the Scalp, Eyelashes and Eyebrows, and which Discourages Hair Loss" and describes a composition for stimulating hair growth in mammals which may include prostaglandins, prostaglandin analogs and combinations thereof.

U.S. Patent Application Publication No. 2007/0231377 to Abou-Nemeh is entitled "Compositions for Promoting Hair Growth" and describes compositions containing methionine analogs and derivatives for promoting hair growth.

U.S. Pat. No. 8,865,144 to Constantinides et al. is entitled "Personal Care Compositions Comprising Responsive Particles" and describes compositions for personal care having polymer based responsive particles.

U.S. Pat. No. 8,715,714 to Kim et al. is entitled "Use of Rare Earth Elements for Hair Improvement" and describes the use of rare earth metals to promote hair growth and treat dandruff.

U.S. Pat. No. 6,800,276 to Kim et al. is entitled "Polyureas and Water-Soluble or Water-Dispersible Polymeric Salts" and describes polymer based cosmetic and pharmaceutical compositions.

Scott's Miracle-Gro® All Purpose Plant Food is a water soluble plant food comprising nitrogen, phosphorus, and potassium in an approximate ratio of 3:1:2 with trace quantities of iron, copper, zinc, manganese, boron, and molybdenum. Scott's Miracle-Gro® African Violet Plant Food is a liquid plant food comprising nitrogen, phosphorus, and potassium in an approximate ratio of 1:1:1 with trace quantities of iron, copper, zinc, manganese, and boron. Miracle-Gro is a registered trademark of The Scotts Miracle-Gro Company.

There exists a need for an effective hair loss composition that is topically active and easy for an individual to use regularly for the requisite period of time to achieve the desired hair growth results without producing unwanted side effects, such as oily or unmanageable hair.

SUMMARY OF THE INVENTION

A composition and method for treatment of hair loss is disclosed that is an effective hair loss composition that is topically active and easy for an individual to use regularly for the requisite period of time to achieve the desired hair growth results without producing unwanted side effects, such as oily or unmanageable hair. The composition comprises a combination of metal and non-metal ions, short chain alcohols and citrus oils. Preferably the composition is formulated as a hair spray for topical application to the scalp, and the metal ions are preferably provided as either water soluble salts or chelated complexes.

A new treatment composition for hair loss is prepared comprising the steps of dissolving or solubilizing treatment components in an aqueous solution, mixing the solubilized components with an alcohol-based solvent, then diluting the mixture with an additional quantity of water to achieve an effective concentration of the active components. The composition is prepared as a non-aerosol hair spray and the hair spray is applied to a user's scalp one to three times per day. A suitable hair spray base preferably comprises short-chain alcohols that are compatible with the treatment components. Additional components suitable for use in a hair spray, such as glycerin, stabilizing agents, or fragrances may be included in the composition.

In addition to promoting hair growth, the disclosed hair spray composition assists with removal of dandruff flakes from the hair and scalp. The hair spray formulation also works to control or manage flyaway hair.

In one embodiment the invention is a composition for treating hair loss comprising water-soluble ionizable metal and non-metal compounds solubilized with aqueous and alcohol-based solvents, solubilized potassium iodide and citrus essential oil.

In another embodiment the invention is a method for making a composition to treat hair loss comprising providing a dry combination of water-soluble ionizable metal and non-metal ionic compounds; mixing said dry combination in a quantity of purified water until a solubilized mixture forms; adding a quantity of a first component comprising an alcohol-based solvent to said solubilized mixture with stirring; adding a quantity of a second component comprising solubilized potassium iodide and kelp extract to said solubilized mixture with stirring; and adding a quantity third of a third component comprising citrus essential oil to said solubilized mixture and stirring until components are fully solubilized.

In yet another embodiment the invention is a method of hair loss treatment comprising the steps of providing a composition having water-soluble ionizable metal and non-metal compounds solubilized with aqueous and alcohol-based solvents, solubilized potassium iodide and citrus essential oil as a non-aerosol spray composition; cleansing a skin area in need of treatment; spraying a first coating of said non-aerosol spray composition to the skin treatment area, said coating being light enough in volume that composition does not run off said skin treatment area; allowing said spray to dry on said skin treatment area; spraying a second coating of said non-aerosol spray composition to said skin area, said coating being light enough in volume that composition does not run off skin treatment area; allowing said second spray to dry on said skin area.

DETAILED DESCRIPTION

Figure 1:
FIG. 1 is a photograph of the scalp crown area of User #1 after using the formulation for 2 years.

A composition for treating hair loss along with a method for making and using the composition is herein disclosed. The composition comprises a combination of metal and non-metal ions, short chain alcohols and citrus oils. Preferably the composition is formulated as a hair spray for topical application to the scalp, and the metal ions are preferably provided as either water soluble salts or chelated complexes. The composition is particularly beneficial for treating hair loss on the scalp, but may be applied to other areas of the skin as well. The composition is useful for remedying hair loss in both men and women.

The hair loss composition is preferably formulated as a hair spray for application to a user's scalp. Preferably the non-aerosol spray will deliver the composition in a light mist to coat the treatment area in such a manner that the composition remains on the treatment area without running off. In an alternative embodiment, the composition may be formulated as a liquid that is applied with a sponge or other means and massaged into the scalp.

Hair growth on the human scalp follows a cycle with three phases—the anagen phase, the catagen phase and the telogen phase.

The anagen (or growth) phase varies by individual and may last anywhere from 2-6 years. In this phase, a hair typically grows at a rate of about 1.25 cm (0.5 inch) per month. Around 85%-90% of the hair on a typical individual's scalp will be in the anagen phase at any given point.

The catagen phase occurs after the anagen phase and during this phase, hair growth ceases. The hair follicle tightens around the hair shaft and the hair root shrinks away from the hair. The catagen phase is a transitional phase lasting around from a few days to a few weeks. Around 4%-5% of the hair on a typical individual's scalp will be in the catagen phase.

During the last or telogen phase, the hair is released from the hair follicle and will eventually fall away from the scalp. After the hair is released, the hair follicle enters a resting phase for around three months. Following this resting phase, the hair growth cycle starts again with the anagen (growth) phase. Around 6%-10% of the hair on a typical individual's scalp will be in the telogen phase. Approximately 80-100 hairs are shed each day, typically just prior to the anagen or growth phase beginning.

Application of the hair loss composition should continue for several months to ensure that all of the hair follicles in the treatment area are in contact with the hair loss composition through all three phases of the hair growth cycle for at least one cycle and preferably through more than one cycle. The hair loss composition is preferably applied to a user's scalp one to three times per day for at least six months to determine efficacy for an individual user.

Preparation of Exemplary Hair Loss Formulations

The hair loss composition invention can be prepared starting with the metal and non-metal ionic components in either a dry form or in a solubilized form. Additional active components are mixed with the ionic compounds and the formulation is diluted to the final volume.

Exemplary Formulation 1—Preparation of Formulation from Dry Components

The formulation of a preferred hair spray composition with the ionic components in a dry form is exemplified below. A dry composition containing metal and non-metal ions is mixed with a quantity of purified water, then mixed with a quantity of alcohol-based solvent. The resultant mixture is combined with a quantity of a solution having solubilized iodine and kelp extract. A quantity of citrus oil is then added to the mixture. Purified water is added to the mixture to reach the final volume desired. Exemplary Formulation 1 will have a final volume of 750 m L.

Step 1: Dry Components

Metal and nonmetal ions useful for the claimed hair product are provided in a dry composition comprised of water-soluble and chelated compounds as characterized in Table I below.

TABLE I

| Ingredient | Total |
| --- | --- |
| Nitrogen, total | 24% |
| Ammoniacal nitrogen 3.5% (as ammonium sulfate) | |
| Urea nitrogen 20.5% (as urea and urea phosphate) | |
| Phosphate, available (as potassium phosphate) | 8% |
| Potassium, soluble (as potash (potassium oxide) and potassium chloride) | 16% |
| Boron (as boric acid) | 0.02% |
| Copper (Cu), soluble (as copper sulfate) | 0.07% |
| Iron (Fe), chelated (as EDTA-Fe) | 0.10% |
| Manganese (Mn), chelated (as EDTA-Mn) | 0.05% |
| Molybdenum (Mo), (as sodium molybdate) | 0.0005% |
| Zinc (Zn), soluble (as zinc sulfate) | 0.06% |

The dry composition of metal and non-metal ions contains excipient ingredients such as binders, thickening agents, and stabilizing agents and combination thereof. The excipient ingredients provide bulk to the dry composition and help to maintain the components in a powder or granular state prior to mixing. The excipient ingredients also assist with solubilizing, suspending or thickening the ionic components after the dry components are solubilized. Stabilizing agents may also increase shelf-life by inhibiting microbial growth in the formulation of solubilized components.

Binders, thickening agents and stabilizing agents are selected from materials that will not react with the metal and non-metal iconic components and which are suitable for a topical skin formulation. Materials may be selected from natural and synthetic water-soluble polymers, soluble silicates, polysaccharides, gums, celluloses, clays, and combinations thereof. Suitable materials include xanthan gum, acacia gum (gum Arabic), guar gum, carrageenan, alginic acid, hydroxyethyl cellulose, methyl cellulose, pectin, starch (rice, wheat or corn derived), aluminum monostearate, polyethylene glycol, sodium silicate, sodium bentonite and attapulgite. Other binders and stabilizing agents that are suitable for topical application and which do not react with the metal and non-metal ionic components may be used in addition to or instead of the agents listed herein.

The concentration of binders and stabilizers is adjusted to achieve a suitable topical formulation that will decrease run-off of the composition from the treatment area, and may vary as needed to achieve a viscosity suitable for a composition formulated as a non-aerosol spray or for a liquid or gel formulation applied by sponge or other application means to the skin treatment area.

Step 2: Solubilizing Dry Components 20 grams to 40 grams of the dry composition characterized in Table I above is vigorously mixed with 60 mL to 120 mL (2-4 ounces) of purified water to solubilize the components. Up to an additional 60 mL to 120 mL of purified water may be added a few milliliters at a time if necessary to fully solubilize the components. The solubilized mixture is then combined with 60 mL to 120 mL of alcohol-based solvent and stirred until a uniform mixture results.

The preferred alcohol-based solvent comprises a short chain alcohol that can be safely applied to human skin. The percentage of short chain alcohol in the alcohol-based solvent is preferably 50% to 70% by volume with the remaining volume comprising purified water. The short chain alcohol is preferably selected from ethyl alcohol, isopropyl alcohol, and combinations thereof. The ethyl alcohol, isopropyl alcohol, and combinations thereof, may further comprise 0.5% methyl salicylate (wintergreen oil). Preferably, the short chain alcohol is 70% isopropyl alcohol.

In a most preferred embodiment, the isopropyl alcohol further comprises 0.5% methyl salicylate (wintergreen oil).

Step 3: Addition of Remaining Active Components

A quantity of a solution having solubilized potassium iodide and kelp extract is added to the mixture prepared in Step 2 and stirred until fully incorporated into the mixture. After the potassium iodide and kelp extract is incorporated into the mixture, a quantity of citrus oil is added and stirred until fully incorporated.

A preferred solution containing potassium iodide and kelp extract has approximately 3-4 mg of solubilized potassium iodide and 40-45 mg of kelp extract per milliliter of solution. An amount ranging from 2 mL to 6 mL of the solubilized potassium iodide/kelp extract may added.

Citrus oil useful for the present formulation is preferably selected from grapefruit essential oil, lemon essential oil, orange essential oil, and combinations thereof. Preferably the citrus oil will have approximately 500 mg to 1000 mg of essential oil per milliliter. A final concentration range of 0.001% to 1.0% of essential oil may be used in the formulation. More preferably, the final concentration is 0.1% to 0.5% by volume.

Step 4: Addition of Purified Water to Finalize Volume

Purified water is added to the resultant mixture from Step 3 to reach the desired final volume of 750 mL and the mixture is stirred to ensure even distribution of the components throughout the composition.

Purified water useful for the composition may be deionized water, distilled water or water that has been filtered to remove particulates and contaminates and would be considered potable. Preferably deionized water is used.

In one preferred embodiment of the hair loss formulation, 20 grams of the dry component mixture is combined with 60 mL purified water and 60 mL of alcohol-based solvent. When the dry components are fully solubilized, 4 mL of potassium iodide/kelp solution and 2 mL of a citrus essential oil are stirred into the mixture and purified water is added to equal 750 mL.

In another preferred embodiment of the hair loss formulation, 40 grams of the dry component mixture is combined with 120 mL purified water and 120 mL of alcohol-based solvent. When the dry components are fully solubilized, 6 mL of potassium iodide/kelp solution and 2 mL of a citrus essential oil are stirred into the mixture and purified water is added to equal 750 mL.

Optional Components

Additional components suitable for use in a hair spray, such as glycerin, gums, water-soluble polymers, stabilizing agents, or fragrances may be optionally included in the hair loss formulation. Components to stabilize the formulation, improve texture and increase shelf life, or fragrances to make it aesthetically agreeable, may be added to the resultant mixture from Step 2 prior to the addition of purified water in Step 4. Purified water is then added to equal 750 mL of solution.

Exemplary Formulation 2—Preparation of Formulation from Solubilized Components

The composition of a preferred hair loss formulation prepared from ionic components provided in a solubilized form is exemplified below. A solubilized composition containing metal and non-metal ions is mixed with a quantity of alcohol-based solvent. The resultant mixture is combined with a quantity of a solution having solubilized iodine and kelp extract. A quantity of citrus oil is then added to the mixture with stirring. Purified water is added to the mixture to reach the final volume desired. Exemplary Formulation 2 will have a final volume of 750 m L.

Step 1: Mixing Solubilized Components with Alcohol-Based Solvent

Metal and nonmetal ions useful for the claimed hair loss composition are provided in a solubilized format comprised of soluble and chelated compounds as characterized in Table II below. The ionic compounds are solubilized in an aqueous base.

TABLE II

| Ingredient | Total |
|---|---|
| Nitrogen, total<br>Ammoniacal nitrogen 0.4% (as ammonium sulfate)<br>Urea nitrogen 6.6% (as urea) | 7% |
| Phosphate, available (as potassium phosphate) | 7% |
| Potassium, soluble (as Potash (Potassium oxide) and Potassium chloride) | 7% |
| Boron (as Boric acid) | 0.02% |
| Copper (Cu), soluble (as Cu-EDTA) | 0.05% |
| Iron (Fe), chelated (as Fe-HEEDTA) | 0.10% |
| Manganese (Mn), chelated (as Mn-EDTA) | 0.08% |
| Zinc (Zn), soluble (as EDTA-Zn) | 0.05% |

A starting quantity of the solubilized ionic mixture of approximately 500 mL is mixed combined with 60 mL to 120 mL of alcohol-based solvent and stirred until a uniform mixture results. The solubilized ionic mixture is thoroughly mixed prior to measuring the starting and finalizing volumes to ensure uniform distribution of the ionic components.

The preferred alcohol-based solvent is a short chain alcohol that can be safely applied to human skin. The percentage of short chain alcohol in the alcohol-based solvent is preferably 50% to 70% by volume with the remaining volume comprising purified water. The short chain alcohol is selected from ethyl alcohol, isopropyl alcohol and combinations thereof. The ethyl alcohol, isopropyl alcohol, and combinations thereof, may further comprise 0.5% methyl salicylate (wintergreen oil). Preferably, the short chain alcohol is 70% isopropyl alcohol. In a most preferred embodiment, the isopropyl alcohol further comprises 0.5% methyl salicylate (wintergreen oil).

Step 2: Addition of Remaining Active Components

A quantity of a solution having solubilized potassium iodide and kelp extract is added to the mixture prepared in Step 1 with stirring. After the potassium iodide and kelp extract is incorporated into the mixture, a quantity of citrus oil is added with stirring.

A preferred solution containing potassium iodide and kelp extract has approximately 3-4 mg of solubilized potassium iodide and 40-45 mg of kelp extract per mL of solution. An amount ranging from 2 mL to 6 mL of the solubilized potassium iodide/kelp may added to the formulation.

Citrus oil useful for the present formulation is preferably selected from grapefruit essential oil, lemon essential oil, orange essential oil, and combinations thereof. Preferably the citrus oil will have approximately 500 mg to 1000 mg of essential per milliliter. A final concentration range of 0.001% to 1.0% of essential oil may be used in the formulation. More preferably, the final concentration is 0.1% to 0.5% by volume.

Step 3: Addition of Solubilized Components to Finalize Volume

After the additional active components in Step 2 have been fully incorporated into the solubilized starting composition, an additional quantity of solubilized components is added to reach a final volume of 750 mL.

Method of Using Hair Loss Formulation

The method of use for treating hair loss will be the same whether the formulation has been prepared using the dry form or solubilized form of the ionic components. The formulation is best dispersed on the scalp when a non-aerosol spray device is employed. A spray device that produces a fine mist is preferred to ensure even distribution to the scalp and to prevent run-off of the formulation from the scalp. A small spray bottle with a 4 to 8 ounce volume capacity is preferred for ease of use. Alternatively, the formulation can be applied to the treatment area with another application means, such as a sponge.

Treatment Step 1: Cleanse Scalp Area

Prior to applying the hair loss formulation, the scalp area should be thoroughly cleansed and then rinsed to remove any soap residue. Hair should be dried prior to application of the formulation. Users should not apply any hair products to the scalp, such as hair spray, gels, mousse or other products as these products may leave a reside on the scalp possibly inhibiting the hair loss formulation from contacting the hair follicles in the treatment area.

Treatment Step 2: Application of Formulation to Scalp

The scalp area is lightly sprayed with the hair loss formulation and the formulation is allowed to dry on the scalp. Care should be taken not to over-spray the treatment area to prevent the formulation from running off the scalp. Once the first spray of the formulation has dried on the scalp, the formulation can be applied to the scalp a second time in a similar manner and allowed to dry. After the second application has dried, the formulation can be applied a third time to the scalp and allowed to dry.

Application of the hair loss formulation according to the above method may be repeated one to two additional times throughout the day. It is not necessary to wash the scalp prior to subsequent treatment applications in a single day.

Application of the hair loss formulation according to the above method should be continued for at least several months to determine individual efficacy and use may be continued long term to maintain hair growth benefit.

Example 1: User #1

A male (User #1) with pronounced hair loss on the crown area of the scalp and moderate hair loss on the frontal area of the scalp applied the hair spray formulation to the entire scalp area two to three times per day for 2 years. The user noticed a marked increase in hair growth on the frontal and crown areas of the scalp.

FIG. 1 shows the crown area of the scalp of User #1 after 2 years of daily use of the formulation. User #1 found that hair around the balding area on the crown was fuller than prior to using the treatment, the diameter of the balding area had decreased, and growth of new hair was evident in the center portion of the balding area on the crown.

Figure 2:
FIG. 2 is a photograph of the frontal area of the scalp of User #1 after using the formulation for 2 years.

FIG. 2 shows the frontal area of the scalp of User #1 after 2 years of daily use of the formulation. User #1 found that hair growth had filled in along the forehead edges where hair had been receding along hairline and hair on the frontal area of the scalp was fuller than prior to using the treatment.

Example 2: User #2

A male (User #2) with substantial hair loss on the frontal, hairline and crown areas of the scalp applied the hair spray formulation to the entire scalp area daily for 6 months. After six months of daily use of the formulation, User #2 found that new hair growth was evident over the balding area in the crown area and saw significant new hair growth on the frontal and forehead portions of the scalp.

I claim:

1. A method of making a composition to treat hair loss comprising:
   solubilizing a first combination of water-soluble ionizable metal compounds consisting of potassium phosphate, potassium oxide, potassium chloride, copper ethylenediaminetretraacetic acid (Cu-EDTA), iron hydroxy-2-ethylenediaminetretraacetic acid (Fe-HEDTA), manganese ethylenediaminetretraacetic acid (Mn-EDTA), zinc ethylenediaminetretraacetic (Zn-EDTA) in a first quantity of purified water;
   solubilizing a second combination of non-metal ionic compounds consisting of ammonium sulfate, urea, and boric acid in a second quantity of purified water; and
   combining said solubilized first combination and said solubilized second combination with mixing to produce a solubilized third combination.

2. The method of claim 1, further comprising:
   adding a quantity of a short chain alcohol to said solubilized third combination.

3. The method of claim 2, wherein said short chain alcohol is selected from ethyl alcohol, isopropyl alcohol, and combinations thereof.

4. The method of claim 3, wherein said quantity of short chain alcohol further comprises methyl salicylate.

5. The method of claim 1, wherein said purified water is distilled or deionized water.

6. The method of claim 1, further comprising:
   adding one or more stabilizing components selected from water-soluble polymers, soluble silicates, polysaccharides, gums, celluloses, clays, xanthan gum, acacia gum, guar gum, carrageenan, alginic acid, hydroxyethyl cellulose, methyl cellulose, pectin, rice starch, wheat starch, corn starch, aluminum monostearate, polyethylene glycol, sodium silicate, sodium bentonite, attapulgite, and combinations thereof, to said first combination of water-soluble ionizable metal compounds prior to solubilizing in water.

7. The method of claim 1, further comprising:
   adding one or more stabilizing components selected from water-soluble polymers, soluble silicates, polysaccharides, gums, celluloses, clays, xanthan gum, acacia gum, guar gum, carrageenan, alginic acid, hydroxyethyl cellulose, methyl cellulose, pectin, rice starch, wheat starch, corn starch, aluminum monostearate, polyethylene glycol, sodium silicate, sodium bentonite, attapulgite, and combinations thereof, to said second combination of water-soluble non-metal ionic compounds prior to solubilizing in water.

* * * * *